United States Patent [19]

Soll et al.

[11] Patent Number: 5,500,442
[45] Date of Patent: Mar. 19, 1996

[54] CYCLOBUT-3-ENE-1,2-DIONE DERIVATIVES AS SMOOTH MUSCLE RELAXANTS

[75] Inventors: Richard M. Soll, Lawrenceville, N.J.; Paul J. Dollings, Newtown; William A. Kinney, Churchville, both of Pa.

[73] Assignee: American Home Products Corporation, Madison, N.J.

[21] Appl. No.: 257,998

[22] Filed: Jun. 10, 1994

[51] Int. Cl.$^6$ .......................... A61K 31/40; C07D 209/34
[52] U.S. Cl. ........................................... 514/414; 548/454
[58] Field of Search .............................. 514/414; 548/454

[56] References Cited

U.S. PATENT DOCUMENTS

| | | | |
|---|---|---|---|
| 4,616,021 | 10/1986 | Ashwood | 514/309 |
| 4,908,378 | 3/1990 | Soll | 514/414 |
| 4,925,839 | 5/1990 | Quagliato | 514/212 |
| 4,983,612 | 1/1991 | Quagliato | 514/300 |
| 5,208,246 | 5/1993 | Almansa | 514/435 |

FOREIGN PATENT DOCUMENTS

| | | | |
|---|---|---|---|
| 0376524 | 7/1990 | European Pat. Off. | C07D 311/68 |
| 0413438 | 2/1991 | European Pat. Off. | C07D 405/04 |
| 0427606 | 5/1991 | European Pat. Off. | C07D 405/04 |
| 0426379 | 5/1991 | European Pat. Off. | C07D 311/68 |

OTHER PUBLICATIONS

Liebeskind and Fengl, J. Org. Chem. 55, 5359–5364 (1990).

*Primary Examiner*—Jacqueline Haley
*Attorney, Agent, or Firm*—R. F. Boswell, Jr.

[57] ABSTRACT

The present invention relates to novel cyclobut-3-ene-1,2-dione-3-yl substituted benzopyrans, indanes and tetrahydronaphthalenones having smooth muscle relaxant activity, pharmaceutical compositions containing them, and to their use in the treatment of diseases and disorders involving excessive smooth muscle contractions in the cardiovascular system, urinary tract, pulmonary system, or gastrointestinal tract.

The compounds of this invention are represented by Formula (I):

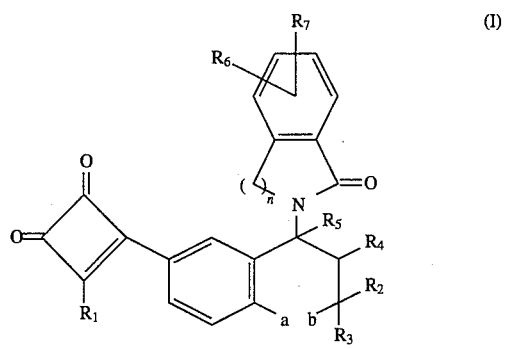

wherein: the substituents are as defined herein.

15 Claims, No Drawings

CYCLOBUT-3-ENE-1,2-DIONE DERIVATIVES AS SMOOTH MUSCLE RELAXANTS

The present invention relates to novel cyclobut-3-ene-1,2-dione-3-yl substituted benzopyrans, indanes and tetrahydronaphthalenones having smooth muscle relaxant activity, pharmaceutical compositions containing them, and to their use in the treatment of diseases and disorders involving excessive smooth muscle contractions in the cardiovascular system, urinary tract, pulmonary system, or gastrointestinal tract such as hypertension, peripheral vascular disease, congestive heart failure, urinary incontinence, irritable bowel syndrome, asthma, and hair loss.

6-Substituted-4-aminobenzopyrans useful in treating hypertension are disclosed in the published PCT patent applications WO 92/19611 and WO 92/20672, published European patent applications EP 0158923 and EP 0427606, and in U.S. Pat. Nos. 4,925,839, 4,908,378 and 4,616,021. 6-Substituted-4-amino tetrahydronaphthalene-1-ones having antihypertensive and bronchodilatory activity are disclosed in U.S. Pat. No. 5,208,246 and in the published European patent application EP 0413438. 5-Substituted-3-aminoindanes useful in treating hypertension and respiratory tract disorders are disclosed in published European patent applications EP 0413438 and EP 0426379. Antihypertensive 6-substituted-4-aminobenzopyrans, tetrahydronaphthalenes or tetrahydroquinolines are disclosed in the published European patent application EP 0376524. None of the above patents or published patent applications disclose benzopyrans, benzonaphthalen-1-ones, or indanes having the cyclobut-3-ene-1,2-dione-3-yl substituent on the benzene portion of the fused rings.

SUMMARY OF THE INVENTION

The present invention discloses compounds represented by the formula (I):

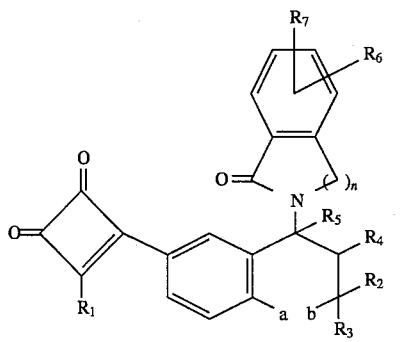

wherein:
$R_1$ is $C_{1-6}$ perfluoroalkoxy, $C_{1-6}$ perfluoroalkyl, $C_{1-6}$ alkyl, $C_{3-10}$ cycloalkyl, $C_{2-6}$ alkenyl, $C_{6-10}$ aryl, H, $C_{1-6}$ alkoxy, hydroxy, $C_{1-6}$ alkoxycarbonyl, amino, pyrrolidine, piperidine, morpholine, $C_{1-12}$ mono or di-alkyl amino optionally substituted with hydroxy or alkoxy, or mono or bicyclic heteroaryl containing 1–3 heteroatoms selected from N, O, or S;
a and b together form an —O— linkage, C=O, or a direct bond;
$R_2$ and $R_3$, independent from each other, are H or $C_{1-6}$ alkyl optionally substituted with fluorine;
either $R_4$ is hydrogen, hydroxy, $C_{1-6}$ alkanoyloxy, $C_{7-11}$ aroyloxy carbamoyloxy, formyloxy, $C_{1-6}$ alkoxycarbonyloxy, mono or di $C_{1-12}$ alkylcarbamoyloxy, and $R_5$ is hydrogen; or $R_4$ and $R_5$ together are a bond;

$R_6$ and $R_7$, independent from each other, are selected from the group consisting of $C_{1-6}$ perfluoroalkoxy, $C_{1-6}$ perfluoroalkyl, $C_{1-6}$ alkyl, $C_{1-6}$ alkoxy, hydroxy, $C_{1-6}$ alkoxycarbonyl, nitro, cyano, halogeno, $C_{1-6}$ alkylsulfonamido, $C_{1-6}$ perfluoroalkylsutfonamido, amino, $C_{1-6}$ acylamino, $C_{1-6}$ perfluoroacylamino, $C_{1-12}$ mono or dialkylamino, $C_{1-6}$ alkylsulfonyl, $C_{6-10}$ arylsulfonyl, carboxyl, $C_{1-12}$ mono or dialkylaminocarbonyl, or hydrogen; and
n=1–3.

The more preferred compounds of this invention are those of Formula I wherein:
$R_1$ is H, $C_{1-6}$ perfluoroalkoxy, $C_{1-6}$ perfluoroalkyl, $C_{1-6}$ alkyl, $C_{3-10}$ cycloalkyl, $C_{6-10}$ aryl, mono and bicyclic heteroaryl containing 1–3 heteroatoms selected from N, O or S; $C_{1-6}$ alkoxy, hydroxy, $C_{1-6}$ alkoxycarbonyl, amino, pyrrolidine, piperidine, morpholine, or $C_{1-12}$ mono or di-alkylamino optionally substitued with hydroxy or alkoxy;
a and b together form an —O— linkage;
$R_2$ and $R_3$, independent from each other, are $C_{1-6}$ alkyl, optionally substituted by fluorine;
either $R_4$ is hydrogen, hydroxy, $C_{1-6}$ alkanoyloxy, or $C_{7-11}$ aroyloxy, and $R_5$ is hydrogen; or $R_4$ and $R_5$ together are a bond;
$R_6$ and $R_7$, independent from each other, are trifluoromethoxy, methoxy, chloro, bromo, fluoro, methyl, trifluoromethyl or H; and
n=1.

The most preferred compounds of this invention are those of Formula I wherein:
$R_1$ is isopropoxy, amino, hydroxyethylamino, pyrrolidinyl, methylamino, hydroxy, or methyl;
$R_2$ and $R_3$ is methyl;
$R_4$ is OH;
$R_5$ is H;
$R_6$ and $R_7$ is H;
n is 1; and
a and b together form an —O— linkage.

The term "mono or bicyclic heteroaryl containing 1–3 heteroatoms selected from N, O, or S" means a compound selected from the group consisting of quinoline, pyridine, indole, pyrrole, quinazoline, pyrazine, pyrimidine, thiophene, furan, benzofuran, benzimidazole, pyrazole, benzoxazole, and benzothiophene. The term alkyl alone or in conjunction with another functional group such as carbonyl, sulfonamido, amino, carbamoyl, sulfonyl or carboxamido encompasses straight and branched chain hydrocarbons such as methyl, ethyl, propyl, isopropyl, butyl, tert-butyl, pentyl, neopentyl, hexyl, decyl, etc. within the limits set forth for the number of carbon atoms. The term perfluoroalkyl means an alkyl group as defined above wherein all of the hydrogen atoms are replaced by fluorine atoms. The term alkoxy means an —O-alkyl group where alkyl is as defined above and a perfluoroalkoxy group is an alkoxy group wherein the alkyl moiety is a perfluoroalkyl group as defined above. The term $C_{6-10}$ aryl means phenyl or naphthyl optionally substituted by halogen, cyano, nitro, $C_{1-6}$ alkyl, $C_{1-6}$ alkoxy, $C_{3-6}$ cycloalkyl and may be used in conjunction with a functional group such as amino, sulfonyl, or oxy. The term $C_{7-11}$ aroyl used alone or in conjunction with another term means phenylcarbonyl or naphthalenylcarbonyl. The term $C_{2-6}$ alkenyl encompasses straight and branched chain alkenes such as vinyl, allyl, 2-methyl allyl, n-butenyl, pentene and hexene. The term $C_{3-10}$ cycloalkyl encompasses mono and bicycloalkyl groups such as cyclopropane, cyclobutane, cyclopentane, cyclohexane, cyclooctane and decalin. The term halogen means fluorine, chlorine, bromine or iodine. The term $C_{1-6}$ alkyl optionally substituted by fluorine means that one or more of the hydrogens of a $C_{1-6}$ alkyl group may be replaced by fluorine, up to and including $C_{1-6}$ perfluoroalkyl groups.

It is understood that the definition of the compounds of formula (I), when $R_4$ is hydroxy and $R_5$ is a hydrogen encompass all possible stereoisomers and mixtures thereof which possess the activity discussed below. In particular, it encompasses racemic modifications and any optical isomers which possess the indicated activity. Optical isomers may be obtained in pure form by standard separation techniques.

The compounds of formula (I) are smooth relaxants. They are therefore useful in the treatment of hypertension as well as for treatment of peripheral vascular disease, congestive heart failure and disorders involving excessive smooth muscle contraction of the urinary tract (such as incontinence), or of the gastro-intestinal tract (such as irritable bowel syndrome), asthma, and hair loss.

The present invention accordingly provides for a pharmaceutical composition which comprises a compound of this invention and a pharmaceutically acceptable carrier. The compositions are preferably adapted for oral administration. However, they may be adapted for other modes of administration, for example parenteral administration for patients suffering from heart failure.

The present invention further provides a compound of the invention for use as an active therapeutic substance. Compounds of formula (I) are of particular use in the treatment of hypertension and/or smooth muscle relaxation.

DETAILED DESCRIPTION OF THE INVENTION

The compounds of the present invention may be prepared by the methodology of Liebeskind el. al. (*J. Org. Chem.* 1990, 55, 5359). More particularly, the compounds of formula (II)

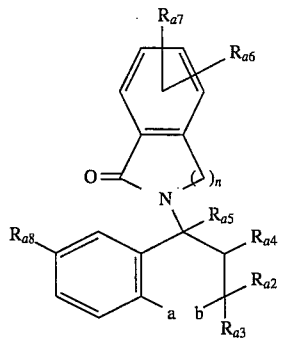

wherein $R_{a8}$ is halogen or trifluromethanesulfonate and $R_{a2}$, $R_{a3}$, $R_{a4}$, $R_{a5}$, $R_{a6}$, and $R_{a7}$ are $R_2$, $R_3$, $R_4$, $R_5$, $R_6$ and $R_7$ respectively, as defined hereinbefore or a group or atom convertible thereto, are reacted with stannane of formula III under

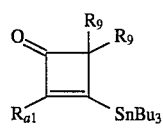

palladium catalysis wherein $R_{a1}$ is typically O-alkyl or alkyl and $R_9$ is O or an acetal to provide a compound of formula IV

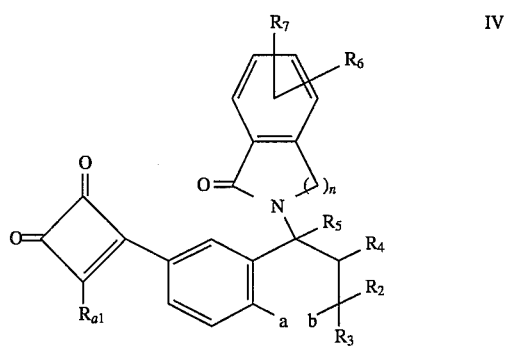

wherein $R_{a1}$ is $C_{1-6}$ alkyl or O-$C_{1-6}$ alkyl. $Ra_1$ may then be convertible to $R_1$ if necessary. For example, when $R_{a1}$ is O-$C_{1-6}$ alkyl, $R_{a1}$ may be converted to hydroxy by treatment with 6 N HCl or converted to amino by treatment with ammonia.

The following specific synthetic examples are illustrative of the methods of preparing compounds of this invention. The corresponding tetrahydro and dihydronaphthalen-1-one, indene and indane analogs can be prepared by one skilled in the an using appropriately substituted tetrahydro and dihydronaphthalene-1-one, indene and indane intermediates prepared according to published procedures.

EXAMPLE 1 trans-4-Amino-3,4-dihydro-2,2-dimethyl-6-iodo-2H-1-benzopyran-3-ol.

To a solution of 10.0g (35 mmol) of 2,2-dimethyl-6-iodo-2H-benzopyran as prepared by Soll et al. (U.S. Pat. No. 4,908,378) in dimethylsulfoxide (98 mL) containing 1.26 mL of water was added 12.4 g (70 mmol) of N-bromosuccinimide. The reaction mixture was stirred for 1 h and was cooled as necessary with an ice bath to prevent an exotherm. The reaction mixture was quenched with water (ca. 250 mL) and then extracted into $Et_2O$. The ethereal extracts were washed with water (3 x), dried over $MgSO_4$ and purified by preparative HPLC (20% $CH_2Cl_2$: 80% hexane to 90% $CH_2Cl_2$: 10% hexane to give 12.7 g (95%) of trans-3-bromo-3,4-dihydro-2,2-dimethyl-6-iodo-2H- 1-benzopyran-4-ol: $^1$H-NMR (DMSO-$d_6$; 300 MHz) δ7.68 (d, 1 H), 7.48 (dd, 1 H), 6.61 (d, 1 H), 6.21 (d, 1 H), 4.74 (t, 1 H), 4.23 (d, 1 H), 1.51 (s, 3 H), and 1.35 ppm (s, 3 H).

To a solution of 12.7 g (33.2 mmol) of this compound in 20% water—dioxane (67 mL) was added NaOH (1.46 g, 36.6 mmol). The reaction mixture was stirred for 8 h and was judged incomplete by tlc. To the reaction was added another 665 mg( 16.6 mmol) of NaOH. After stirring at ambient temperature for 3 days, the reaction mixture was quenched with water (200 mL) and then was extracted into ether. The ethereal extracts were dried over $K_2CO_3$ and then concentrated to give 9.78 g (98% yield) of cis-3,4-epoxy-3,4-dihydro-2,2-dimethyl-6-iodo-2H-1-benzopyran as a yellow oil which was used without further purification: 1H-NMR (DMSO-$d_6$; 300 MHz) δ7.83 (d, 1 H), 7.54 (dd, 1 H), 6.59 (d, 1 H), 4.04 (d, 1 H), 3.70 (d, 1 H), 1.45 (s, 3 H), and 1.18 ppm (s, 3 H).

To a solution of 5.18 g (17.2 retool) of the epoxide prepared above in ethanol (155 mL) was added 155 mL of ammonium hydroxide. After stirring for 8 h at ambient temperature, another 155 mL of ammonium hydroxide was added. The reaction mixture was stirred at ambient temperature for 3 days. The reaction mixture was diluted with saturated NaCl solution and then was extracted into 20% THF/CH$_2$Cl$_2$. The organic extracts were dried over K$_2$CO$_3$ and concentrated to give 5.48 g of the title compound which was used without further purification: $^1$H-NMR (DMSO-d$_6$; 300 MHz) δ7.84 (d, 1 H), 7.37 (dd, 1 H), 6.53 (d, 1 H), 5.44 (br d, 1 H), 3.49 (d, 1 H), 3.32 (br s, 1 H), 3.16 (dd, 1 H), 2.5 (br s, 2 H), 1.35 (s, 3 H), and 1.07 ppm (s, 3 H).

EXAMPLE 2 trans-2-[2,3-Dihydro-2,2-dimethyl-3-hydroxy-6-iodo-4H- 1-benzopyran-4-yl]-2,3-dihydro-1H-isoindol-1-one.

To a solution of 5.48 g (17.2 mmol) of trans-4-amino-3, 4-dihydro-2,2-dimethyl- 6-iodo-2H-1-benzopyran-3-ol as prepared in Example 1 in methanol (34 mL) containing 3.38 g (20.6 mmol) of 2-carbomethoxybenzaldehyde was added 68.7 mL (34.4 mmol) of 0.5 M zinc chloride-modified sodium cyanoborohydride in methanol, prepared according to the method of Kim et. al. *L. Org. Chem.* 50 (11), 1927 (1985). The reaction mixture was refluxed for 3 h, cooled to room temperature and quenched with water (375 mL). The reaction mixture was extracted into 20% THF/CH$_2$Cl$_2$, and the extracts were dried over MgSO$_4$. Purification was achieved by flash chromatography (CH$_2$Cl$_2$:MeOH:NH$_4$OH (94.75: 3.5: 1.75) to give 7.07 g of the title compound as a white solid. An analytical sample, mp 224°–228° C., was obtained by additional flash chromatography using (25% Et$_2$O-CH$_2$Cl$_2$): $^1$H-NMR (DMSO-d$_6$; 300 MHz) δ7.79 (d, 1 H), 7.53–7.68 (m, 3 H), 7.46 (dd, 1 H), 7.02 (s, 1 H), 6.67 (d, 1 H), 5.75 (d, 1 H), 5.1 (bs, 1 H), 4.5 (br d, 1 H), 4.1 (br, d 1 H), 3.89 (br, 1 H), 1.45 (s, 3 H), and 1.22 ppm (s, 3 H); mass spectrum (CI), m/e 436, 435, 417, 402. Anal. Calcd. for C$_{19}$H$_{18}$INO$_3$. 1 H$_2$O: C, 51.36; H, 4.31; N, 3.15 Found: C, 51.62; H, 4.04; N, 2.95.

EXAMPLE 3

3-[trans-3-hydroxy-2,2-dimethyl-4-(1-oxo-1,3-dihydroisoindol-2-yl)-chroman-6-yl]-4-isopropoxy-cyclobut-3-ene-1,2-dione.

To a solution of 217 mg (0.50 retool) of trans-2-[2,3-dihydro-2,2-dimethyl- 3-hydroxy-6-iodo-4H-1-benzopyran-4-yl]-2,3-dihydro-1H-isoindol-1-one, prepared in Example 2, and 235 mg (0.55 mmol) of 3-(1-methylethoxy)-4-(tri-n-butylstannyl)- 3-cyclobutene-1,2-dione, as prepared by Liebeskind et. al. (J. Org. Chem. 55, 5359 (1990)), in DMF (620 μL) was added 23 mg (0.03 mmol) of trans-benzyl(chloro-)bis(trisphenyl-phosphine) palladium (II) and 8.5 mg (0.04 mmol) of copper (I) chloride. After stirring at ambient temperature for 1.5 h, the reaction mixture was dissolved in hot CH$_3$CN (200 mL) and was washed with hexane. The acetonitrile phase was dried over MgSO$_4$ and was concentrated to a solid, which was then dissolved in hot THF/CH$_2$Cl$_2$ and absorbed onto silica gel. Purification by flash chromatography (65% EtOAc/35% hexane) gave 36 mg (16% yield) of the title compound. Additional compound was prepared in a repeat reaction in 52% yield by purifying with a short flash chromatography column using (CH$_3$CN elution). Repeated crystallizations from CH$_3$CN/Et$_2$O/hexane provided an analytically pure sample, mp> 250° C.: $^1$H-NMR (DMSO-d$_6$; 400 MHz) δ7.83 (d, 1 H), 7.78 (dd, 1 H), 7.54– 7.66 (m , 3 H), 7.38 (s, 1 H), 7.05 (d, 1 H), 5.86 (d, 1 It), 5.32 (br d, 1 H), 5.24 (septet, 1 H), 4.47–4.48 (br d, 1 H), 3.9–4.1 (br, 2 H), 1.51 (s, 3 H), 1.29 (s, 3 H), 1.25 (d, 3 H), and 1.02 ppm (d, 3 H); mass spectrum (DEI) m/e 447,429, 414. Anal. Calcd. for C$_{26}$H$_{25}$NO$_6$. 0.5 H$_2$O: C, 68.41; H, 5.74; N, 3.07 Found: C, 68.31; H, 5.56; N, 3.08.

EXAMPLE 4

4-Amino-3-[trans-3-hydroxy-2,2-dimethyl-4-(1-oxo-1,3-dihydroisoindol-2-yl)-chroman-6-yl]-cyclobut-3-ene-1,2-dione.

To a solution of 154 mg (0.344 mmol) of 3-[trans-3-hydroxy-2,2-dimethyl-4-(1-oxo- 1,3-dihydroisoindol-2-yl)-chroman-6-yl]-4-isopropoxy-cyclobut-3-ene-1,2-dione as prepared in Example 3 in CH$_3$CN was bubbled ammonia gas for 30 min. The reaction mixture was then sealed and stirred for 16 h. The reaction mixture was concentrated. Flash chromatography (CH$_2$Cl$_2$: MeOH: NH$_4$OH (94.75/3.5/1.75)) followed by crystallization from THF and petroleum ether gave 136 mg of the title compound as a white solid, mp>250° C.: 1H-NMR (DMSO-d$_6$; 400 MHz) δ8.90 (br s, 1 H), 8.76 (br s, 1 H), 7.7–7.8 (m, 3 H), 7.51–7.63 (m, 3 H), 6.98 (d, 1 H), 1.48 (s, 3 H), and 1.27 ppm (s, 3 H); IR (KBr) 1780, 1730, 1670, and 1640 cm$^{-1}$; mass spectrum (+ CI), m/e 405. Anal. Calcd. for C$_{23}$H$_{20}$N$_2$OS: C, 68.31; H, 4.98; N, 6.93 Found.: C, 67.91; H, 5.12; N, 6.78.

EXAMPLE 5

3-[trans-3-Hydroxy-2,2-dimethyl-4-(1-oxo-1,3-dihydroisoindol-2-yl),-chroman-6-yl]-4-(2-hydroxy-ethylamino)-cyclobut-3-ene-1,2-dione.

A solution of 529 mg( 1.18 mmol) of 3-[trans-3-hydroxy-2,2-dimethyl-4-(1-oxo- 1,3-dihydroisoindol-2-yl)-chroman-6-yl]-4-isopropoxy-cyclobut-3-ene- 1,2-dione as prepared in Example 3 in CH$_3$CN (20 mL) and ethanolamine (716 μL; 11.8 mmol) was stirred at room temperature for 4 days. The reaction mixture was heated at 50° C. for 1 h, cooled to room temperature, diluted with H$_2$O, and extracted into 20% THF/CH$_2$Cl$_2$. The organic extracts were dried over MgSO$_4$ and purified by flash chromatography (CH$_2$Cl$_2$: MeOH :NH$_4$OH (93.25; 4.5; 2.25)) followed by trituration from MeOH/ether to give 124 mg of the title compound as a tan solid, mp 205°–215° C.: $^1$H-NMR (DMSO-d$_6$; 400 MHz) δ8.93 (t, 1 H), 7.79 (dd, 1 H), 7.74 (s, 1 H), 7.69 (dd, 1 H), 7.5–7.64 (m, 3 H), 7.00 (d, 1 H), 5.75 (d, 1 H), 5.2–5.5 (br, 1 H), 4.86 (t, 1 H), 4.4–4.5 (br d, 1 H), 3.67 (m, 2 H), 3.53 (q, 3 H), and 1.27 ppm (s, 3 H); IR (KBr) 1780, 1710, 1660, and 1600 cm$^{-1}$; mass spectrum (+FAB), m/e 449 (M + H), and 471 (M+Na). Anal. Calcd. for C$_{25}$H$_{24}$N$_2$O$_6$. 1 H$_2$O C, 64.37; H, 5.62; N, 6.01 Found: C, 64.32; H, 5.83; N, 6.18.

EXAMPLE 6

3-[trans-3-Hydroxy-2,2-dimethyl-4-(1-oxo-1,3-dihydroisoindol-2-yl)-chroman-6-yl]-4-pyrrolindin-1-yl-cyclobut-3- ene-1,2-dione.

A solution of 413 mg (0.922 mmol) of 3-[trans-3-hydroxy-2,2-dimethyl-4-( 1-oxo-1,3-dihydroisoindol-2-yl)-chroman-6-yl]-4-isopropoxy-cyclobut-3-ene-1,2-dione as prepared in Example 3 in CH$_3$CN (9 mL) and 385 μL (4.61 mmol) of pyrrolidine was stirred at room temperature for 16 h. The reaction mixture was diluted with pH 7 buffer and was extracted into 20% THF/CH$_2$Cl$_2$. The organic extracts were dried (MgSO$_4$) and combined with the crude product from an identical run using 205 mg of starting material. The combined crude products were dissolved in 50% THF/ MeOH, absorbed onto silica gel, and purified by flash chromatography ($CH_2Cl_2$:MeOH:$NH_4OH$ (93.25/4.5/2.25)) and then re-chromatographed (85% EtOAc/hexane) to give 323 mg of the title compound. An analytical sample, mp>250° C., was obtained by recrystallization from THF/ petroleum ether to give 278 mg of product: $^1$H-NMR (DMSO-$d_6$; 400 MHz) δ7.80 (dd, 1 H), 7.71 (dd, 1 H), 7.54–7.67 (m, 3 H), 7.09 (br s, 1 H), 6.97 (d, 1 H), 5.80 (d, 1 H), 5.3 (br s, 1 H), 3.75 (t, 2H), 3.14– 3.19 (m, 1 H), 3.02–3.05 (m, 1 H), 1.62–1.76 (m, 2 H), 1.49 (s, 3 H), 1.41–1.44 (m, 1 H), 1.27 (s, 3 H), and 1.17–1.19 ppm (m, 1 H); IR (KBr) 1770, 1720, 1665, and 1595 cm$^{-1}$; mass spectrum (-FAB), m/e 457 (M–H), 324, and 132. Anal. Calcd. for $C_{27}H_{26}N_2O_5$. 0.25 $H_2O$: C, 70.04; H, 5.77; N, 6.05 Found: C, 69.95; H, 5.84; N, 5.85.

EXAMPLE 7

3-[trans-3-Hydroxy-2,2-dimethyl-4-(1-oxo-1,3-dihydroisoindol-2-yl)-chroman-6-yl]-4-methylamino-cyclobut-3-ene-1,2-dione.

A solution of 408mg (0.911 mmol) of 3-[trans-3-hydroxy-2,2-dimethyl-4-( 1-oxo-1,3-dihydroisoindol-2-yl)-chroman-6-yl]-4-isopropoxy-cyclobut-3-ene-1,2-dione as prepared in Example 3 in $CH_3CN$ (9 mL) and 569 μL (4.55 mmol) of 8.0 M methylamine in ethanol was stirred at room temperature for 6 h. The reaction mixture was diluted with pH 7 buffer and then extracted into 20% THF/$CH_2Cl_2$. The crude product was dissolved in a little MeOH, absorbed onto silica gel, and purified by flash chromatography ($CH_2Cl_2$:MeOH:$NH_4OH$ (92.5/5/2.5)) to give 296 mg of pure product. Recrystallization from THF/petroleum ether gave 187 mg of the title compound as a white solid, mp>250° C.: $^1$H-NMR (DMSO-$d_6$; 400 MHz) δ8.84 (q, 1 H), 7.79 (d, 1 H), 7.71 (s, 1 H), 7.51–7.67 (m, 3 H), 6.99 (d, 1 H), 5.75 (d, 1 H), 3.22 (d, 3 H), 1.48 (s, 3 H), and 1.27 ppm (s, 3 H); IR (KBr) 1770, 1720, 1670, and 1605 cm$^{-1}$; mass spectrum (+FAB),m/e 419 (M+H), 441 (M+Na). Anal. Calcd. for $C_{24}H_{22}N_2O_5$ . 0.25 $H_2O$: C, 68.16; H, 5.36; N, 6.62 Found: C, 68.22; H, 5.33; N, 6.54.

EXAMPLE 8

3-Hydroxy-4-[trans-3-hydroxy-2,2-dimethyl-4-(1-oxo-1,3-dihydroisoindol-2-yl)-chroman-6-yl]-cyclobut-3-ene-1,2-dione.

A solution of 303 mg (0.676 retool) of 3-[trans-3-hydroxy-2,2-dimethyl-4-(1- oxo-1,3-dihydroisoindol-2-yl)-chroman-6-yl]-4-isopropoxy-cyclobut-3-ene-1,2-dione in THF (5 mL) containing 1.13 mL (6 N HCl) was heated at 50° C. for 48 h. The reaction mixture was diluted with 2 N HCl and extracted into 20% THF-$CH_2Cl_2$. The combined organic extracts were dried (MgSO$_4$), concentrated, and recrystallized from THF to give 112 mg of the title compound as a tan solid, mp>250° C.: $^1$H-NMR (DMSO-$d_6$; 400 MHz) δ7.84 (dd, 1 H), 7.81 (d, 1 H), 7.52–7.64 (m, 3 H), 7.51 (s, 1 H), 6.93 (d, 1 H), 5.3 (br s, 1 H), 4.4–4.5 (br d, 1 H), 3.8–4.1 (br, 2 H), 1.47 (s, 3 H), and 1.26 ppm (s, 3 H); IR (KBr) 3400, 1785, 1720, 1670, and 1600 cm$^{-1}$; mass spectrum (DCI+), m/e 406 (M+H). Anal. Calcd. for $C_{23}H_{19}NO_6$. 0.5 $H_2O$: C, 66.66; H, 4.86; N, 3.38 Found: C, 66.67; H, 4.60; N, 3.34.

EXAMPLE 9

3-[trans-3-Hydroxy-2,2-dimethyl-4-(1-oxo-1,3-dihydro-isoindol-2-yl)-chroman-6-yl]-4-methyl-cyciobut-3-ene-1,2-dione.

A solution of 275 mg (0.631 mmol) of trans-2-[2,3-dihydro-2,2-dimethyl-3-hydroxy- 6-iodo-4H-1-benzopyran-4-yl]-2,3-dihydro-1H-isoindol-1-one as prepared in Example 1 in DMF 800 μL containing 10.8 mg (0.056 mmol) of copper (I) iodide, 28.7 mg (0.038 mmol) of trans-benzyl(chloro)bis(triphenylphospine) palladium (II), and 325 mg (0.758 mmol) of 3-(tri-n-butylstannyl)-4-methyl-3-cyclobutene-1,2-dione 2-(ethylene acetal), as prepared by Liebeskind el. al. (J. Org. Chem. 55, 5359 (1990), was purged with $N_2$, and then stirred at room temperature for 16 h. The reaction mixture was diluted with 20% THF-$CH_2Cl_2$ (50 mL), washed with sat. aq. $NH_4Cl$, and then 10% KF. The organic phase was dried over $Na_2SO_4$, concentrated, and purified by flash chromatography ($CH_2Cl_2$:MeOH:$NH_4OH$ (94.75/3.5/1.75)) to give 298 mg of 3-[trans-3-hydroxy-2,2-dimethyl-4-(1-oxo-1,3-dihydro-isoindol-2 -yl)-chroman-6-yl]-4-methyl-cyclobut-3-ene-1,2-dione 2-(ethylene acetal) which was used directly in the next reaction: partial $^1$H-NMR (DMSO-$d_6$; 300 MHz) δ 7.83 (d, 1 H), 7.53–7.66 (m, 5 H), 5.89 (d, 1 H), 5.2–5.4 (br d, 1 H), 4.4–4.6 (br d, 1 H), 1.89 (s, 3 H), 1.52 (s, 3 H), and 1.30 ppm (s, 3 H).

To a solution of 276 mg (0.616 retool) of 3-[trans-3-hydroxy-[2,2-dimethyl-4-( 1-oxo- 1,3-dihydro-isoindol-2-yl)-chroman-6-yl]-4-methyl-cyclobut-3-ene-1,2-dione-2-(ethylene acetal) in THF (12 mL) was added 9.2 mL of 50% aqueous. $H_2SO_4$ The reaction mixture was stirred at room temperature for 2 h. The reaction mixture was diluted with 50 mL of $H_2O$ and then extracted into 20% THF-$CH_2Cl_2$. The organic extract was dried ($Na_2SO_4$), concentrated, and combined with the crude product from a similar run using 264 mg of 3-[trans-3-hydroxy-]2,2-dimethyl-4-(1-oxo-1,3-dihydroisoindol- 2-yl)-chroman-6-yl]-4-methyl-cyclobut-3-ene-1,2 dione 2-(ethylene acetal). Purification by flash chromatography ($CH_2Cl_2$:MeOH:$NH_4OH$ (95.5/3/1.5)) and crystallization from THF/petroleum ether gave 268 mg of the title compound as a pale yellow solid, mp>250° C.: 7.81–7.84 (two doublets, 2 H), 7.53–7.66 (m, 4 H), 7.09 (d, 1 H), 5.87 (d, 1 H), 5.3–5.4 (br s, 1 H), 4.5 (br d, 1 H), 2.36 (s, 3H), 1.52 (s, 3 H), and 1.29 ppm (s, 3 H); IR (KBr) 1775, 1760, 1660, and 1610 cm$^{-1}$; mass spectrum (DCI+) m/e 404 (M+H). Anal. Calcd. for $C_{24}H_{21}NO_5$: C, 71.45; H, 5.25; N, 3.47 Found: C, 71.21; H, 5.23; N, 3.26.

Pharmacology

Bladder smooth muscle relaxing activity of the compounds of this invention was established in accordance with standard pharmaceutically accepted test procedures in representative compounds as follows:

Sprague-Dawley rats (150–200 g) are rendered unconscious by $CO_2$ asphyxiation and then euthanized by cervical dislocation. The bladder is removed into warm (37 deg. C) physiological salt solution (PSS) of the following composition (mM): NaCl, 118.4; KCl, 4.7; $CaCl_2$, 2.5; $MgSO_4$, 4.7; $H_2O$, 1.2; $NaHCO_3$, 24.9; $KH_2PO_4$, 1.2; glucose, 11.1; EDTA, 0.023; gassed with 95% $O_2$; 2/5% $CO_2$; pH 7.4. The bladder is opened and then cut into strips 1–2 mm in width and 7–10 mm in length. The strips are subsequently suspended in a 10 ml tissue bath under an initial resting tension of 1.5 g. The strips are held in place by two surgical clips one of which is attached to fixed hook while the other is attached to an isometric force transducer. The preparations, which usually exhibit small spontaneous contractions, are allowed to recover for a period of 1 hour prior to a challenge with 0.1 µM carbachol. The carbachol is then washed out and the tissue allowed to relax to its resting level of activity. Following 1 further 30 min period of recovery an additional 15 mM KCl are introduced into the tissue bath. This increase in KCl concentration results in a large increase in the amplitude of spontaneous contractions (and initiation of contractions in previously quiescent strips) superimposed upon a small increase in basal tone. Following stabilization of this enhanced level of contractile activity, incremental increases in the concentration of test compound or vehicle are introduced into the tissue bath. Contractile activity is measured for each compound or vehicle concentration during the last rain of a 30 rain challenge.

Isometric force developed by the bladder strips is measured using a concentration required to elicit 50% inhibition of pre-drug contractile activity ($IC_{50}$ concentration) is calculated from this concentration-response curve. The maximum percentage inhibition of contractile activity evoked by a test compound is also recorded for concentrations of test compound<or equal to 30 uM.

Aortic smooth muscle relaxing activity of the compounds of this invention was established in accordance with standard pharmaceutically accepted test procedures in representative compounds as follows:

Sprague-Dawley rats (150–200 g) are rendered unconscious by $CO_2$ asphyxiation and then euthanized by cervical dislocation. The thoracic aorta is removed into warm (37 deg. C.) Krebs-Henseleit solution. The aorta is cleaned of fat and loose adventitia and cut into rings 3–4 mm in width. The rings are subsequently suspended between two stainless steel wire tissue holders in a 10 ml tissue bath. One wire tissue holder is attached to fixed hook while the other is attached to an isometric force transducer. Resting tension is set at 1.0 g. The tissues are allowed to recover for a period of 60 mins prior to beginning the experiment. The tissues are challenged with 25 mM KCl to elicit a contracture. The tissue are then washed repeatedly with fresh Krebs-Henseleit solution over a period of 30 rains and allowed to recover to baseline tension. 25 mM KCl is then introduced into the tissue bath to evoke a contracture that is allowed to stabilize for not less than 45 rains. Increasing concentrations of test compound or vehicle are then added to the tissue bath in a cumulative fashion.

Isometric force developed by the aortic rings is measured using force transducer and recorded on a polygraph. The percentage inhibition of contractile force evoked by each concentration of a given test compound is used to generate a concentration-response curve. The concentration required to elicit 50% inhibition of pre-drug contractile activity ($IC_{50}$ concentration) is calculated from this concentration-response curve. The maximum percentage inhibition of contractile activity evoked by a test compound is also recorded for concentrations of test compound<or equal to 30 uM.

Pharmacological test data are presented in Table I.

TABLE I

Inhibition of Contractions in Isolated Rat Bladder and Aortic Tissue

| Compound | $IC_{50}$ or (% Inhibition of Bladder Contraction at 30 µM) | $IC_{50}$ or (% Inhibition of Aorta Contraction at 30 µM) |
|---|---|---|
| Example 3 | 10.1 ± 0.39 µM | 1.16 ± 0.21 µM |
| Example 4 | 0.19 ± 0.02 µM | 0.17 ± 0.04 µM |
| Example 5 | (14%) | N.D. |
| Example 6 | (33%) | N.D. |
| Example 7 | 1.62 µM | 0.83 ± 0.24 µM |
| Example 8 | 21.9 µM | N.D. |
| Example 9 | 0.11 µM | 0.015 ± 0.007 µM |

N.D.: not determined.

Hence, the compounds of this invention have a pronounced effect on smooth muscle contractility and are useful in the treatment of hypertension, urinary incontinence, irritable bladder and bowel disease, asthma, stroke and similar disease states as mentioned above, which are amenable to treatment with compounds by administration, orally, parenterally, or by aspiration to a patient in need thereof.

Pharmaceutical Composition

When the compounds of the invention are employed in the treatment of diseases or disorders associated with smooth muscle contractions, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may also be injected intravenously or parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol. The compounds may also be formulated into dry aerosol inhalation formulations.

The dosage requirements vary with the particular compositions employed, the route of administration, the severity of the symptoms presented and the particular subject being treated. Treatment will generally be initiated with small dosages, less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single dose, or if desired, the dosage may be divided into convenient subunits administered at suitable times throughout the day.

What is claimed is:

1. A compound according to the formula:

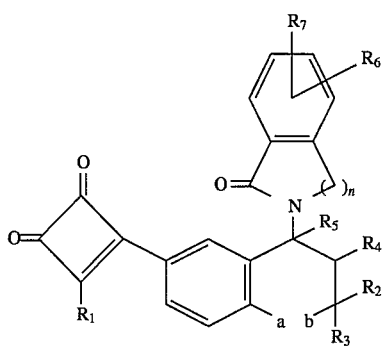

wherein:

R₁ is $C_{1-6}$ perfluoroalkoxyl, $C_{1-6}$ perfluoroalkyl, $C_{1-6}$ alkyl, $C_{3-10}$ cycloalkyl, $C_{2-6}$ alkenyl, $C_{6-10}$ aryl, H, $C_{1-6}$ alkoxy, hydroxy, $C_{1-6}$ alkoxycarbonyl, amino, pyrrolidine, piperidine, morpholine, $C_{1-12}$ mono or di-alkylamino optionally substituted with hydroxy or $C_{1-6}$ alkoxy, or mono or bicyclic heteroaryl selected from quinoline, pyridine, indole, pyrrole, quinazoline, pyrazine, pyrimidine, thiophene, furan, benzofuran, benzimidazole, pyrazole, benzoxazole, and benzothiophene;

a and b together form an —O— linkage, C=O, or a direct bond;

R₂ and R₃, independent from each other, are H or $C_{1-6}$ alkyl, optionally substituted by fluorine;

either R₄ is hydrogen, hydroxy, $C_{1-6}$ alkanoyloxy, $C_{7-11}$ aroyloxy, carbamoyloxy, $C_{1-6}$ alkoxycarbonyloxy, mono or di $C_{1-12}$ alkylcarbamoyloxy, and R₅ is hydrogen; or R₄ and R₅ together are a bond;

R₆ and R₇, independent from each other, are selected from the group consisting of $C_{1-6}$ perfluoroalkoxy, $C_{1-6}$ perfluoroalkyl, $C_{1-6}$ alkyl, $C_{1-6}$ alkoxy, hydroxy, $C_{1-6}$ alkoxycarbonyl, nitro, cyano, halogeno, $C_{1-6}$ alkylsulfonamido, $C_{1-6}$ perfluoroalkylsulfonamido, amino, $C_{1-6}$ acylamino, $C_{1-6}$ perfluoroacylamino, $C_{1-2}$ mono or di-alkylamino, $C_{1-6}$ alkylsulfonyl, $C_{6-10}$ arylsulfonyl, carboxy, $C_{1-12}$ mono or dialkylaminocarbonyl, and hydrogen;

and n is 1 to 3.

2. A compound according to claim 1 wherein:

R₁ is hydrogen, $C_{1-6}$ perfluoroalkoxy, $C_{1-6}$ perfluoroalkyl, $C_{1-6}$ alkyl, $C_{6-10}$ aryl, $C_{1-6}$ alkoxy, hydroxy, $C_{1-6}$ alkoxycarbonyl, amino, pyrrolidine, piperidine, morpholine, $C_{1-12}$ mono or di-alkylamino optionally substituted with hydroxy or $C_{1-6}$ alkoxy, or mono or bicyclic heteroaryl selected from quinoline, pyridine, indole, pyrrole, quinazoline, pyrazine, pyrimidine, thiophene, furan, benzofuran, benzimidazole, pyrazole, benzoxazole, and benzothiophene;

a and b together form an —O— linkage;

R₂ and R₃, independent from each other, are hydrogen or $C_{1-6}$ alkyl, optionally substituted by fluorine;

either R₄ is hydrogen, hydroxy, $C_{1-6}$ alkanoyloxy, or $C_{7-11}$ aroyloxy, and R₅ is hydrogen; or R₄ and R₅ together are a bond;

R₆ and R₇, independent from each other, are trifluoromethoxy, methoxy, chloro, bromo, fluoro, methyl, trifluoromethyl or H; and n=1.

3. A compound according to claim 2 wherein:

R₁ is isopropoxy, amino, hydroxyethylamino, pyrrolidinyl, methylamino, hydroxy, or methyl;

R₂ and R₃ are methyl;

R₄ is OH;

R₅ is H;

R₆ and R₇ are H;

n is 1; and a and b together form an —O— linkage.

4. A compound according to claim 3 which is 3-[trans-3-hydroxy-2,2-dimethyl- 4-(1-oxo-1,2-dihydroisoindol-2-yl)-chroman-6-yl]-4-isopropoxy-cyclobut-3-ene- 1,2-dione.

5. A compound according to claim 3 which is 4-amino-3-[trans-3-hydroxy- 2,2-dimethyl-4-(1-oxo-1,3-dihydroisoindol-2-yl)-chroman-6-yl]-cyclobut-3-ene-1,2-dione.

6. A compound according to claim 3 which is 3-[trans-3-hydroxy-2,2-dimethyl-4-( 1-oxo-1,3-dihydroisoindol-2-yl)-chroman-6-yl]-4-(2′-hydroxy-ethylamino)-cyclobut-3-ene-1,2-dione.

7. A compound according to claim 3 which is 3-[trans-3-hydroxy-2,2-dimethyl-4-( 1-oxo-1,3-dihydroisoindol-2-yl)-chroman-6-yl ]-4-pyrrolindin-1-yl-cyclobut-3-ene- 1,2-dione.

8. A compound according to claim 3 which is 3-[trans-3-hydroxy-2,2-dimethyl-4-( 1-oxo-1,3-dihydroisoindol-2-yl)-chroman-6-yl]-4-methylamino-cyclobut-3-ene- 1,2-dione.

9. A compound according to claim 3 which is 3-hydroxy-4-[trans-3-hydroxy-2,2-dimethyl- 4-(1-oxo-1,3-dihydroisoindol-2-yl)-chroman-6-yl]-cyclobut-3-ene- 1,2-dione.

10. A compound according to claim 3 which is 3-[trans-3-Hydroxy-2,2-dimethyl-4-( 1-oxo-1,3-dihydro-isoindol-2-yl)-chroman-6-yl]-4-methyl-cyclobut-3-ene-1,2-dione.

11. A method of treating a diseases associated with the regulation of smooth muscle contractions in the cardiovascular, respiratory, gastrointestinal, or urinary systems which comprises administration to a mammal in need thereof of a therapeutically effective amount of a compound represented by the formula:

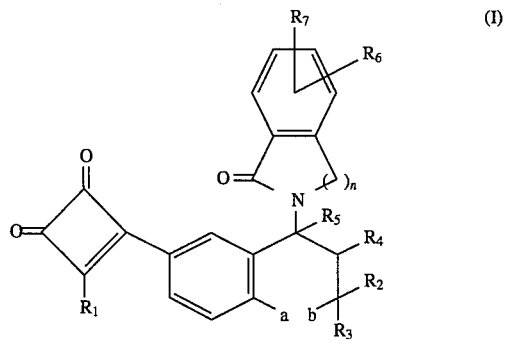

(I)

wherein:

R₁ is $C_{1-6}$ perfluoroalkoxyl, $C_{1-6}$ perfluoroalkyl, $C_{1-6}$ alkyl, $C_{3-10}$ cycloalkyl, $C_{2-6}$ alkenyl, $C_{6-10}$ aryl, H, $C_{1-6}$ alkoxy, hydroxy, $C_{1-6}$ alkoxycarbonyl, amino, pyrrolidine, piperidine, morpholine, $C_{1-12}$ mono or di-alkylamino optionally substituted with hydroxy or $C_{1-6}$ alkoxy, or mono or bicyclic heteroaryl selected from quinoline, pyridine, indole, pyrrole, quinazoline, pyrazine, pyrimidine, thiophene, furan, benzofuran, benzimidazole, pyrazole, benzoxazole, and benzothiophene;

R₂ and R₃, independent from each other, are hydrogen or $C_{1-6}$ alkyl, optionally substituted by fluorine;

either R₄ is hydrogen, hydroxy, $C_{1-6}$ alkanoyloxy, $C_{7-11}$ aroyloxy, carbamoyloxy, $C_{1-6}$ alkoxycarbonyloxy, mono or di $C_{1-12}$ alkylcarbamoyloxy, and R₅ is hydrogen; or R₄ and R₅ together are a bond;

R₆ and R₇, independent from each other, are selected from the group consisting of $C_{1-6}$ perfluoroalkoxy, $C_{1-6}$ perfluoroalkyl, $C_{1-6}$ alkyl, $C_{1-6}$ alkoxy, hydroxy, $C_{1-6}$ alkoxycarbonyl, nitro, cyano, halogeno, $C_{1-6}$ alkylsulfonamido, $C_{1-6}$ perfluoroalkylsulfonamido, amino, $C_{1-6}$ acylamino, $C_{1-6}$ perfluoroacylamino, $C_{1-12}$ mono or di-alkylamino, $C_{1-6}$ alkylsulfonyl, $C_{6-10}$ arylsulfonyl, carboxy, $C_{1-12}$ mono or dialkylaminocarbonyl, or hydrogen; and n=1–3.

12. A method according to claim 11 wherein the compound is selected from those having the formula:

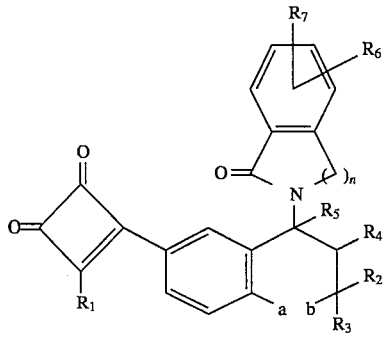

wherein:

$R_1$ is hydrogen, $C_{1-6}$ perfluoroalkoxy, $C_{1-6}$ perfluoroalkyl, $C_{1-6}$ alkyl, $C_{6-10}$ aryl, $C_{1-6}$ alkoxy, hydroxy, $C_{1-6}$ alkoxycarbonyl, amino, pyrrolidine, pipeddine, morpholine, $C_{1-12}$ mono or di-alkylamino optionally substituted with hydroxy or $C_{1-6}$ alkoxy, or mono or bicyclic heteroaryl containing 1–3 selected from quinoline, pyridine, indole, pyrrole, quinazoline, pyrazine, pyrimidine, thiophene, furan, benzofuran, benzimidazole, pyrazole, benzoxazole, and benzothiophene;

a and b together form an —O— linkage;

$R_2$ and $R_3$, independent from each other, are hydrogen or $C_{1-6}$ alkyl, optionally substituted by fluorine;

either $R_4$ is hydrogen, hydroxy, $C_{1-6}$ alkanoyloxy, or $C_{6-12}$ aroyloxy, and $R_5$ is hydrogen; or $R_4$ and $R_5$ together are a bond;

$R_6$ and $R_7$, independent from each other, are trifluoromethoxy, methoxy, chloro, bromo, fluoro, methyl, trifluoromethyl or H; and n=1.

13. The method according to claim 12 wherein the compound is selected from those having the formula

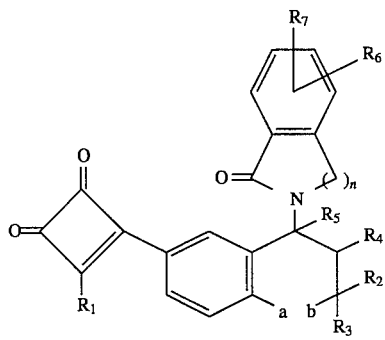

wherein $R_1$ is isopropoxy, amino, hydroxyethylamino, pyrrolidinyl, methylamino, hydroxy or methyl;

$R_2$ and $R_3$ is methyl;

$R_4$ is OH;

$R_5$ is H;

$R_6$ and $R_7$ is H;

n is 1; and a and b together form an —O— linkage.

14. A method according to claim 13 wherein the compound is selected from: 3-[trans-3-hydroxy-2,2-dimethyl-4-(oxo- 1,2-dihydroisoindol-2-yl)-chroman-6-yl] -4-isopropoxy-cyclobut-3-ene-1,2-dione, 4-amino-3-[trans-3-hydroxy-2,2-dimethyl-4-(1-oxo-1,3-dihydroiso-indol-2-yl)-chroman-6-yl]-cyclobut-3-ene- 1,2-dione, 3-[trans-3-hydroxy-2,2-dimethyl-4-(1-oxo-1,3-dihydroisoindol-2-yl))-chroman- 6-yl]-4-(2-hydroxy-ethylamino)-cyclobut-3-ene-1,2-dione, 3-[trans-3-hydroxy-2,2-dimethyl-4-( 1-oxo- 1,3-dihydroisoindol-2-yl)-chroman- 6-yl]-4-pyrrolindin-1-yl-cyclobut-3-ene-1,2-dione, 3-[trans-3-hydroxy-2,2-dimethyl-4-(1-oxo-1,3-dihydroisoindol-2-yl)-chroman- 6-yl]-4-methylamino-cyclobut-3-ene-1,2-dione, 3-hydroxy-4-[trans-3-hydroxy-2,2-dimethyl-4- (1-oxo-1,3-dihydroisoindol- 2-yl)-chroman-6-yl]-cyclobut-3-ene-1,2-dione, and 3- [trans-3-Hydroxy-2,2-dimethyl-4- ( 1 -oxo- 1,3-dihydro-isoindol- 2-yl)-chroman-6-yl]-4-methyl-cyclobut-3-ene- 1,2-dione.

15. A pharmaceutical composition for the treatment of a disease or disorder attributed to smooth muscle contraction which comprises a pharmaceutically acceptable carrier and a therapeutically effective amount of a compound of the formula

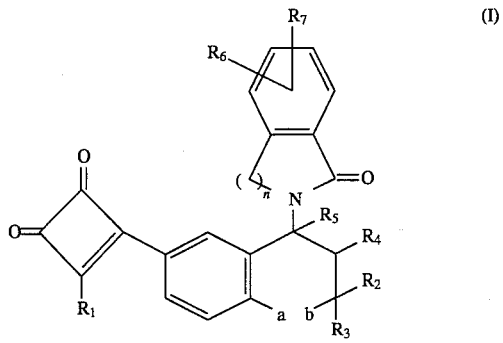

(I)

wherein:

$R_1$ is $C_{1-6}$ perfluoroalkoxyl, $C_{1-6}$ perfluoroalkyl, $C_{1-6}$ alkyl, $C_{3-10}$ cycloalkyl, $C_{2-6}$ alkenyl, $C_{6-10}$ aryl, H, $C_{1-6}$ alkoxy, hydroxy, $C_{1-6}$ alkoxycarbonyl, amino, pyrrolidine, piperidine, morpholine, or $C_{1-12}$ mono or di-alkylamino optionally substituted with hydroxy or $C_{1-6}$ alkoxy, or mono or bicyclic heteroaryl selected from quinoline, pyridine, indole, pyrrole, quinazoline, pyrazine, pyrimidine, thiophene, furan, benzofuran, benzimidazole, pyrazole, benzoxazole, and benzothiophene;

a and b together form an —O— linkage, C=O, or a direct bond;

$R_2$ and $R_3$, independent from each other, are hydrogen or $C_{1-6}$ alkyl, optionally substituted by fluorine;

either $R_4$ is hydrogen, hydroxy, $C_{1-6}$ alkanoyloxy, $C_{7-11}$ aroyloxy carbamoyloxy, $C_{1-6}$ alkoxycarbonyloxy, mono or di $C_{1-12}$ alkylcarbamoyloxy, and $R_5$ is hydrogen; or $R_4$ and $R_5$ together are a bond;

$R_6$ and $R_7$, independent from each other, are selected from the group consisting of $C_{1-6}$ perfluoroalkoxy, $C_{1-6}$ perfluoroalkyl, $C_{1-6}$ alkyl, $C_{1-6}$ alkoxy, hydroxy, $C_{1-6}$ alkoxycarbonyl, nitro, cyano, halogeno, $C_{1-6}$ alkylsulfonamido, $C_{1-6}$ perfluoroalkylsulfonamido, amino, $C_{1-6}$ acylamino, $C_{1-6}$ perfluoroacylamino, $C_{1-12}$ mono or di-alkylamino, $C_{1-6}$ alkylsulfonyl, $C_{6-10}$ arylsulfonyl, carboxy, $C_{1-12}$ mono or dialkylaminocarbonyl, or hydrogen; and n=1–3.

* * * * *